Figure 1:
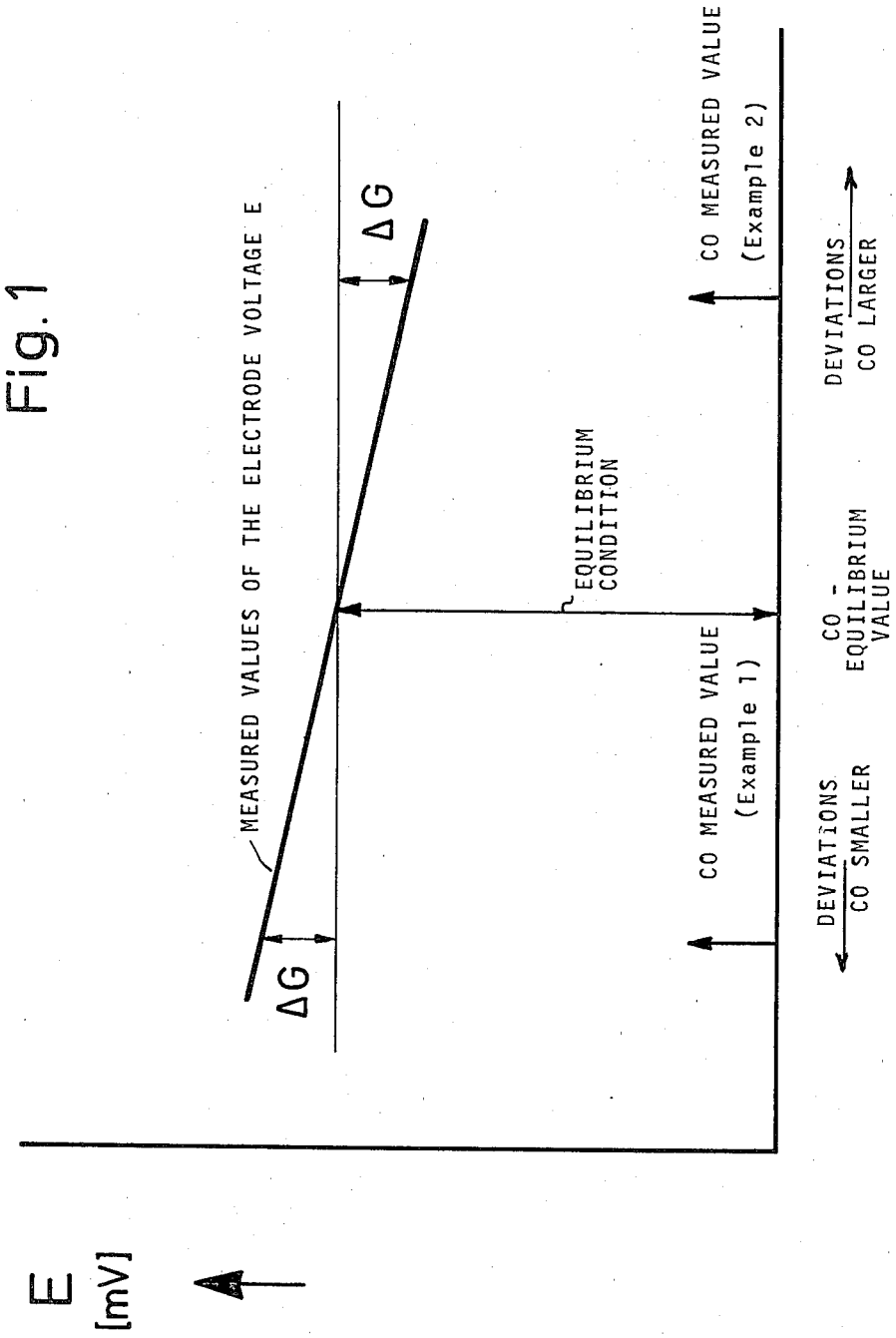

United States Patent [19]

Göhring et al.

[11] 4,372,790

[45] Feb. 8, 1983

[54] METHOD AND APPARATUS FOR THE CONTROL OF THE CARBON LEVEL OF A GAS MIXTURE REACTING IN A FURNACE CHAMBER

[75] Inventors: Werner Göhring, Kleve, Fed. Rep. of Germany; Cornelius H. Luiten, Nijmegen, Netherlands

[73] Assignee: Ipsen Industries International GmbH, Kleve, Fed. Rep. of Germany

[21] Appl. No.: 21,375

[22] Filed: Mar. 19, 1979

[30] Foreign Application Priority Data

Mar. 21, 1978 [CH] Switzerland .................. 3114/78

[51] Int. Cl.$^3$ ............................................. C21D 1/48
[52] U.S. Cl. .................................... 148/16.5; 148/16; 148/16.6; 148/20.3
[58] Field of Search ................... 148/16, 16.5, 16.6, 148/20.3

[56] References Cited

U.S. PATENT DOCUMENTS

| | | | |
|---|---|---|---|
| 4,035,203 | 7/1977 | L'Hermite et al. | 148/16.5 |
| 4,049,473 | 9/1977 | Davis et al. | 148/16.5 |
| 4,145,232 | 3/1979 | Solomon | 148/16.5 |
| 4,191,598 | 3/1980 | Conybear et al. | 148/16.5 |

OTHER PUBLICATIONS

"Practical Experience in the Control of Heat Treatment Atmosphere Using the Oxygen Probe", N. Beach, 5th ed. Ind. Proc. Heat Conf., 1972.

"Control of Carbon Potential in Heating Atmosphere Using a Carbon Sensor", Blumenthal et al., ASM Heat Treating Conf., Chicago, 9/75.

*Primary Examiner*—John P. Sheehan
*Attorney, Agent, or Firm*—Martin A. Farber

[57] ABSTRACT

A method and device for control of the carbon level of a gas mixture reacting in a heat treatment furnace, which gas mixture arises by means of the introduction of a fuel containing hydrocarbon into the furnace chamber, the reaction products of which are not in a state of water-gas equilibrium and not in a state of methane gas equilibrium and which gas mixture has an excess of methane. The controlled condition is determined by a first measurement device from the portion of the gas component CO which is present in the furnace chamber as a first measured value, and by a second measurement device from the electrical voltage of an oxygen-ion-conducting solid body electrolyte as a second measured value and by a third measurement device from the furnace chamber temperature as the third measured value. A regulating member is controlled as a result to automatically change the quantity flow of the supply to the furnace chamber until correspondence of the measured carbon level with its desired value exists.

1 Claim, 5 Drawing Figures

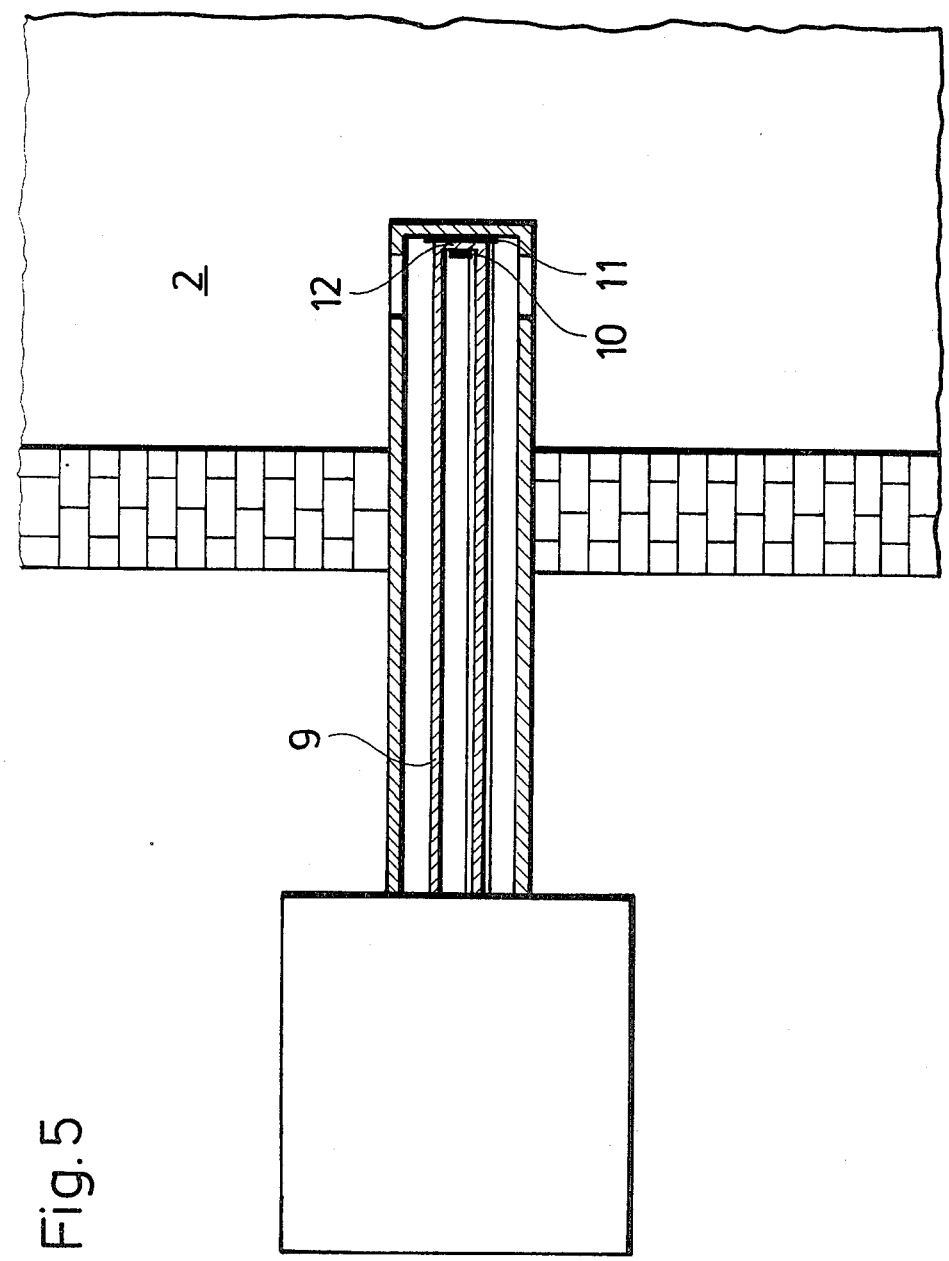

METHOD AND APPARATUS FOR THE CONTROL OF THE CARBON LEVEL OF A GAS MIXTURE REACTING IN A FURNACE CHAMBER

The invention relates to a method for control of the carbon level of a gas mixture reacting in a heat treatment furnace, which gas mixture arises through the introduction of a hydrocarbon-containing fuel into a furnace chamber, the reaction products of which are not in a state of water-gas equilibrium and not in a state of methane gas equilibrium and which gas mixture exhibits an excess of methane. The invention further relates to an apparatus for carrying out this method.

Under the known carburization methods the gas carburization as well as the carbonnitriding and bare hardening (Blankhärten) in furnace atmospheres of similar type have gained increasing significance. The methods are performed in heat treatment furnaces of closed construction, which permit a controlled atmosphere to be adjusted or set and to be maintained at a certain reaction temperature. The essential problem or difficulty of the gas caburization method resides in performing transmission of the carbon from the gas atmosphere to the steel material in a controlled manner in order to achieve reproduceable carburization results on workpieces of different basic carbon content, different alloys as well as different shape.

It is known to introduce a fuel-air mixture into the furnace chamber for the formation of a furnace atmosphere, which mixture is not in the state of equilibrium. By corresponding mixing of a hydrocarbon containing fuel and air one can produce effective carburization gases. On the basis of the fact that in the furnace chamber these are not in a state of water-gas equilibrium and not in a state of methane gas equilibrium, it is unfortunately difficult to detect or determine and to control the carbon level. It has been attempted to perform a direct determination of the carbon level with the help of foil- or wire- probes which are suspended in the furnace chamber, which probes after a treatment time of approximately 30 minutes are taken from the furnace and then are inspected for their carbon content. The carbon pick-up of the probes in this manner can be determined discontinuously. An automatic process control is not possible.

On the basis of the described disadvantages this simple method, known for decades, for the production of a carburization atmosphere was displaced by the use of protective gas generators which make possible the production of a furnace atmosphere in chemical equilibrium, the carbon level of which furnace atmosphere is automatically controllable, in the manner that indirect methods for the process control are used. In this manner the composition of the gas phase is used as a basis for indicating the carbon level. Basic for this, however, is the presence of a chemical equilibrium of the furnace atmosphere, in order with use of the known chemical equilibrium relationships to obtain temperature-dependent characteristic quantities, which quantities can be used as the basis for the process control. In this manner it is known to transmit and monitor constantly the values for carbon monoxide, carbon dioxide, hydrogen and water from the furnace atmosphere, and, based on these variables or controlled conditions, to draw conclusions about the carbon level.

It is disadvantageous in so doing that generators must be used for the production of the useable gas mixtures, which mixtures are in a state of chemical equilibrium. Beyond that it is disadvantageous that the chemical equilibrium condition cannot be maintained in the furnace operation since for the increase of the carbon supply it is necessary to introduce into the furnace chamber a fuel or combustible containing hydrocarbon in addition to the equilibrium gas. The gas mixture then reacting in the furnace chamber reaches the water-gas equilibrium only insufficiently and has in any case an excess of methane. The instant the carburizing atmosphere is made available or has been prepared with sufficient carbon supply in the furnace, the equilibrium condition necessary for the known control or arrangement, no longer exists. The reaction degree of the gas mixture in the furnace chamber depends on many variable factors, such as furnace temperature, furnace-chamber size and contact duration or residence time of the mixture, gas circulation, catalytic action or rust formation in the furnace chamber, type of the fuel and/or respectively of the existing oxygen, etc. Under practical conditions, at best an approximation of the water-gas equilibrium is to be counted on. A considerable excess of non-reacting hydrocarbon remains in any case. Consequently the carbon level of the reacting gas mixture cannot be determined with the necessary exactness by the usual measurement of the $CO_2$ or $H_2O$ portion of the furnace atmosphere.

The invention is based on the task to find a continuous measured quantity (or quantity to be measured) and variable quantity or controlled carbon level of a fuel-air mixture-furnace atmosphere, which quantity and variable do not have the existence of a chemical equilibrium as a precondition. Particularly with use of indirect quantities to be measured of the furnace atmosphere, an automatic control of the carbon level should be able to be achieved even with strong $CH_4$ excess of the furnace atmosphere. Moreover it is the aim of the invention to propose a device with which such an automatic control of the furnace atmosphere can be carried through in a simple manner.

In a method of the type mentioned in the introduction, the task is solved in accordance with the invention, in the manner that the variable or controlled carbon level is determined from the portion of the gas component CO which is present in the furnace chamber as of a first quantity to be measured, from the electrical voltage of an oxygen-ion-conducting solid body electrolyte as of a second quantity to be measured and from the furnace chamber temperature as of a third quantity to be measured. Other than according to the state of the technology according to which the carbon level of a furnace atmosphere can only be determined if there is a chemical equilibrium, with the aid of a function $pCO^2/pCO_2$, according to the invention the carbon level of a reacting gas mixture which is not in equilibrium is determined in the manner that additionally to the measurement of the CO quantity portion as a quantity to be measured, the electrical voltage of an oxygen-ion-conducting solid body electrolyte is incorporated, which voltage represents the free reaction enthalpy which is still present in the furnace atmosphere.

It is known that the electrical voltage of an oxygen-ion-conducting solid body electrolyte in the equilibrium condition indicates the portion of oxygen-containing gases in the gas mixture. It was recognized that in the reacting condition the voltage also additionally determines the free energy necessary for the attainable restoration or establishment of equilibrium. The free energy ΔG is a function of the product of the Faraday constant F with the electrode potential E. It amounts to ΔG=RT/4F(ln pCO measured value − ln pCO equilibrium value) [mV]

FIG. 1 explains the relationship: On the ordinate the voltage E of the solid body electrolyte is illustrated. The measured values are composed of a voltage portion for the equilibrium condition and a voltage portion for the free energy ΔG. The CO values are illustrated on the abscissa. The vertical line in the center over the CO equilibrium value characterizes the equilibrium condition. To the left of it are tabulated the equilibrium deviations toward smaller CO measured values and to the right of it toward larger measured CO values. The previously mentioned fixed relationship between the free reaction enthalpy, the measured CO value and the CO equilibrium value, permits a conversion to equilibrium values on the basis of the measured values to be used in accordance with the invention. The determination of the carbon level with the aid of or from the equilibrium values as such is known.

Suitably the method of the invention is carried out such that the three measured values of the furnace atmosphere are measured, are fed to a computer for determining the carbon level from the three measured values and depending on this, the quantity or mass flow of the combustion material and/or of the air introduced into the furnace space is changed until correspondence or agreement of the measured carbon level with its nominal or desired value is produced, for which purpose quantity or mass flows of combustion gas and/or air are exclusively supplied to the furnace chamber. In this manner the carbon level and therewith the speed of the carburization, the layer thickness as well as the carbon distribution in the surface layer zone can be automatically controlled. By the constant comparison of the measured values, by means of the computer, with the specified or prescribed nominal or desired value of the carbon level, by means of the variation or change of the quantity (or mass) flows, an exceptional precision and reproducability of the adjustment or setting of the carbon level is achieved. The previously employed preparation, treatment or separation of the furnace atmosphere in separate protective gas generators is avoided.

The device for performing the described method in accordance with the invention is characterized by a first measuring device for the continuous determination of the CO content of the furnace atmosphere, a second measuring device comprising a solid body electrolyte on a zirconium oxide base, which solid body electrolyte is arranged in the furnace chamber, by a temperature measuring device as well as a computer for determining the carbon level from the three measured values, by means of which a regulating or setting member is controlled, which member automatically changes the quantity flow of the fuel or combustion material, and/or of the air introduced into the furnace space chamber, until there is correspondence or conformity of the measured carbon level with its desired value. Advantageous embodiments of this device are claimed in the dependent claims.

Figure 2:
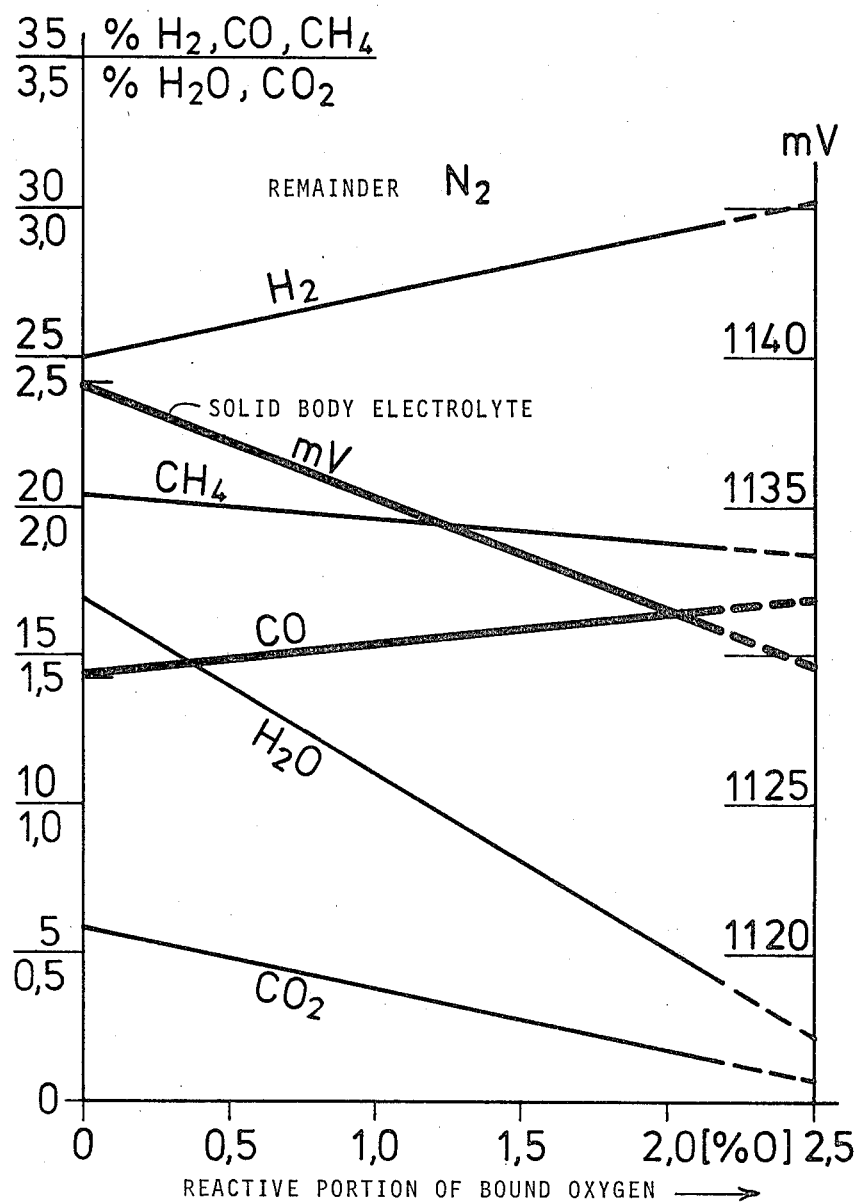
Figure 3:
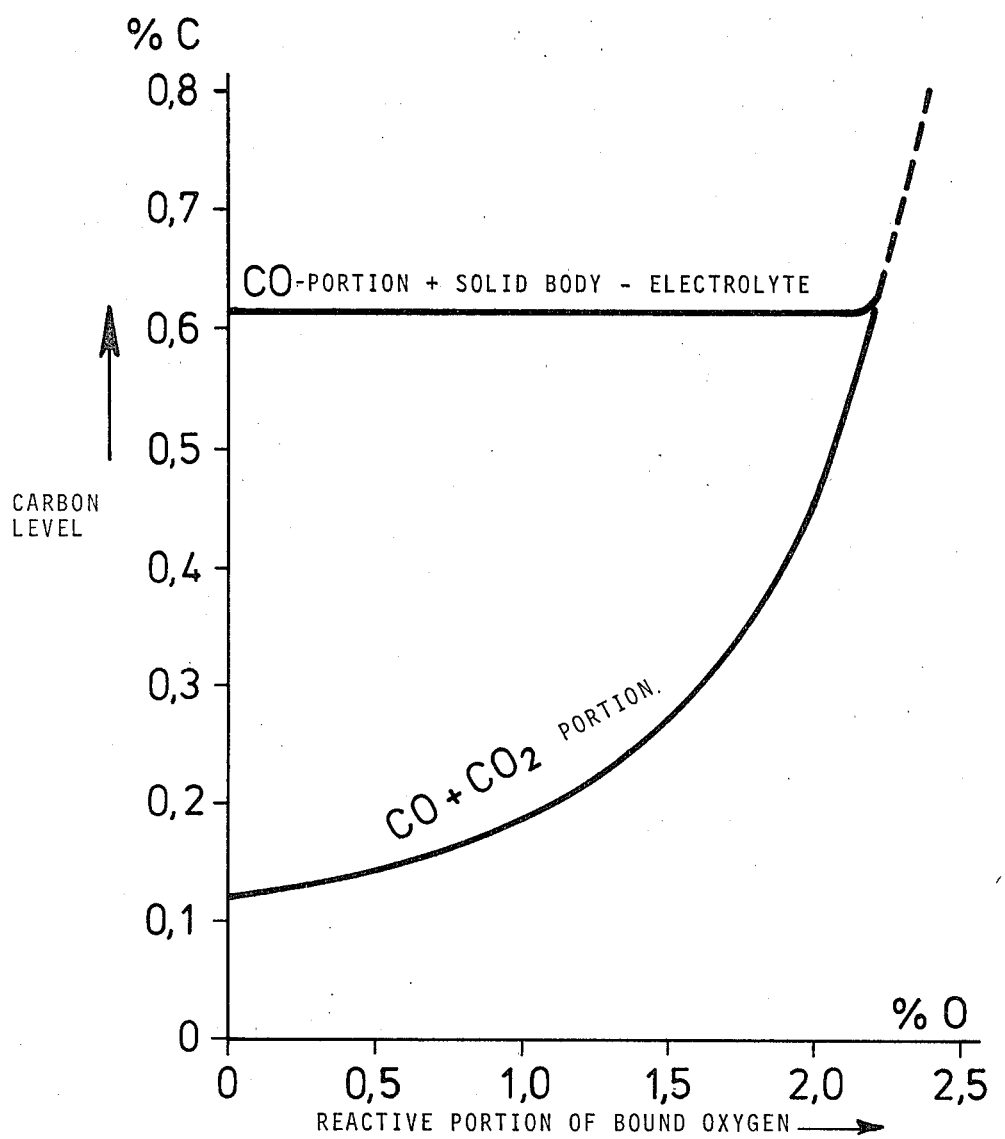
Figure 4:
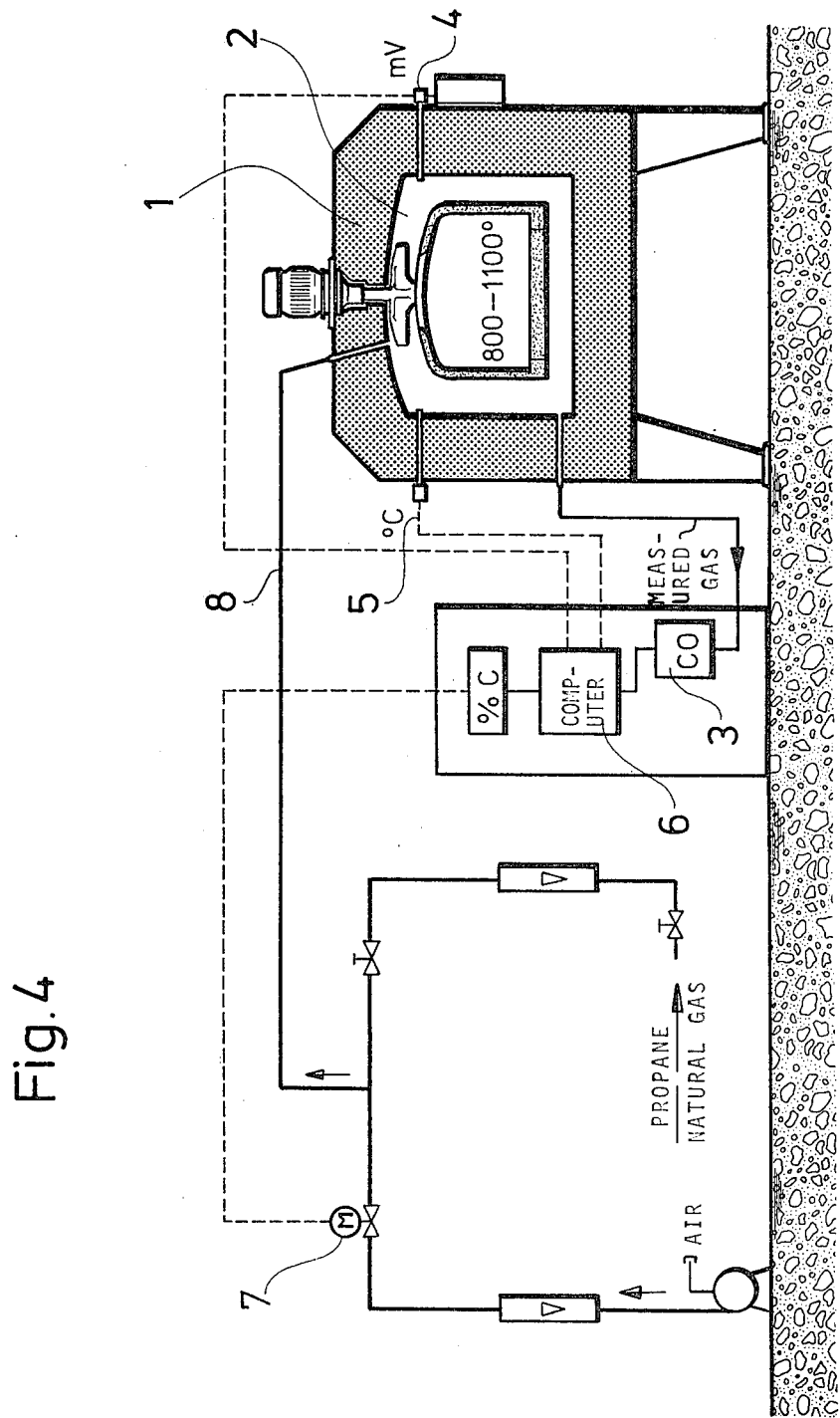

In the following the invention is described on the basis of embodiment examples with reference to the drawing. In the drawing:

FIG. 1 shows a schematic diagram, which illustrates the dependency of the voltage of a solid body electrolyte on furnace atmospheres not in the equilibrium condition, FIG. 2 shows the composition of a controlled furnace atmosphere at different reaction degree, FIG. 3 shows the evaluation of measured values with changing reaction degree, FIG. 4 schematically shows a control device, and FIG. 5 shows an oxygen probe in the section of a furnace wall.

EXAMPLE 1

The first example relates to a furnace atmosphere which comprises a combustion gas mixture which has high $CO_2$— and $H_2O$— portions and the carbon level of which is considerably too low. Such a furnace atmosphere can arise by penetration of air into the furnace chamber or during a purging or cleaning operation. The furnace atmosphere should be brought to a carbon level of 0.62% C by addition of natural gas and consequently is not in the condition of chemical equilibrium. The following measured values or quantities of the furnace atmosphere result during the controlled addition of natural gas:

| | |
|---|---|
| Furnace temperature | 930 degrees C. |
| Voltage on the solid body electrolyte | 1138 mV |
| CO volume portion | 14.5% |
| $CO_2$ volume portion | 0.59% |
| $H_2O$ volume portion | 1.7% |
| $CH_4$ volume portion | 20.5% |
| $H_2$ volume portion | 25.0% |
| $N_2$ volume portion | Remainder |

In FIG. 2 the composition of the controlled furnace atmosphere at different reaction rate or degree is illustrated, as it can occur during or with furnace operation of longer duration. The gas volume portions of the furnace atmosphere and the voltage on the solid body electrolyte (reference gas air) are illustrated on the ordinate. The abscissa illustrates the reactive portion of bound oxygen. The previously named measured quantities are to be assumed or adopted as the zero point of the reactive oxygen portion. With longer residence time or contact duration of the gas mixture in the furnace chamber or under the influence of a catalytic action or effect, the reaction degree or rate increases, characterized by the reactive oxygen portion. The oxygen is given off from or by $CO_2$ and $H_2O$ and reacts with excessive $CH_4$ to CO. The increase of the $CO_2$ portion corresponds quantitatively to the reactive portion of the bound oxygen.

In FIG. 3 the evaluation of the measured values with changing reaction rate is illustrated. The carbon level is indicated on the ordinate, and on the abscissa the same reactive portion of bound oxygen as in FIG. 2 is indicated.

The curve shows the ascertained or determined carbon level from the CO— and $CO_2$— portions. The straight line shows the course of the carbon level with the determination in accordance with the invention, from the CO portion and the voltage of an oxygen-ion-conducting solid body electrolyte at the indicated temperature. The comparison shows clearly the erroneous determination on the basis of the $CO/CO_2$ quantity portions according to the state of the technology and the independency of the method in accordance with the invention from the equilibrium setting or equilibrium restoration.

The evaluation of the measured values in the furnace atmosphere results in the following carbon levels:

| | |
|---|---|
| according to the known method with employment of the measured CO— and CO2— portions | 0.12% C |
| according to the invention with use of the measured CO— portion and of the voltage of the solid body electrolyte | 0.615% C |
| by the way of comparison with use of the measured CO2 portion and of the voltage of the solid body electrolyte | 1.98% C |

An examination of these values with the aid of the foil probe gave a carbon level of 0.62% C. The result shows clearly that the method in accordance with the invention permits an exact determination of the carbon level in spite of considerable deviations of the furnace atmosphere from the water gas equilibrium and from the methane equilibrium and varying or changing reaction rate. With the actual carbon level, according to the water gas equilibrium at a CO portion of 14.5%, the $CO_2$ portion should amount to only 0.1%. The methane portion corresponding to the equilibrium amounts to 0.0065% $CH_4$ at 930 degrees C. furnace temperature. The actually present $CH_4$ portion exceeds this value by more than 3150 times.

With a particularly preferred embodiment example of the invention quantity flow streams of fuel and air are exclusively supplied to the furnace chamber. The advantage is that for the production of the furnace atmosphere neither a protective gas generator for the preparation or treatment of a fuel-air mixture nor nitrogen from a supply container is required. In addition to these savings of apparatus and energy, the combustion heat of the fuel-air mixture in the furnace chamber can be utilized.

The following describes a second embodiment relating to this preferred embodiment:

EXAMPLE 2

In a furnace chamber with a volume of approximately 1 m$^3$ at 850 degrees C., quantity flow streams of $V_n=2.0$ m$^3$ natural gas and $V_n=2.5$ m$^3$ air are introduced.

The gas mixture which reacts in the furnace chamber yields the following measured values:

| | |
|---|---|
| Voltage on the solid body electrolyte | 1133 mV |
| CO volume portion | 17.2% |
| CO2 volume portion | 0.115% |
| H2O volume portion | 0.4% |
| CH4 volume portion | 4.5% |
| H2 volume portion | 43.5% |
| N2 volume portion | remainder |

The carbon levels determined from the measured values amount to:

| | |
|---|---|
| with the method in accordance with the invention: | |
| CO + electrolyte | 0.92% C |
| By way of comparison: | |
| from CO + CO2 | 1.34% C |
| from CO2 + electrolyte | 1.60% C |
| The carbon level actually determined at several foil probes amounts to an average | 0.925% C |

FIG. 4 of the drawings shows a device for the performance of the method, which device is connected to a furnace 1, which furnace is schematically illustrated. The furnace 1 has a closed working chamber 2, in which temperatures of 800 to 1,100 degrees C. can be set. A first measuring device 3 is connected to the working chamber 2, with which measuring device 3 measuring gas from the furnace atmosphere can be removed and fed to a CO analyzer, the latter determining the CO portion of the furnace atmosphere according to the infrared absorption principle. Moreover a second measuring device 4 is arranged on the furnace, the measuring device 4 comprising a solid body electrolyte arranged or set on a zirconium oxide base, the electrolyte being arranged in the furnace chamber, the outer electrode 11 of the solid body electrolyte being in connection with the furnace atmosphere and its inner electrode 10 standing in connection with air, as FIG. 5 of the drawing illustrates in greater detail. A voltage mV is obtained as a measured value.

Moreover a third measuring device 5 for the continuous determination of the furnace chamber temperature is connected to the furnace chamber 2. All three measured quantities are fed into a computer 6 for the determination of the carbon level. The computer is an electronic module or chip programmed according to its purpose, which module digitally indicates the actual carbon level. This is expressed by the symbol %C in the drawing.

A positioning or control member 7 is connected to the computer 6, the control member 7 being controlled in dependency on the carbon level, the control member 7 varying or changing the quantity flow stream of the combustion gases and/or of the air fed or introduced into the furnace chamber until there is correspondence or agreement of the measured carbon level with its nominal or desired value. The arrangement of the line for air as well as propane gas and natural gas, respectively, is schematically illustrated in the drawing. The feed or supply takes place by means of a conduit or tubing 8.

In principle the solid body electrolyte (second measuring device 4) according to FIG. 5 of the drawing comprises a wall 9 made of stabilized zirconium oxide. One side of the wall 9 is in contact with a reference gas with known oxygen content, in the present case air, and is conductively connected with an electrode 10, which subsequently is referred to as the inner electrode. The other side of the wall 9 is in contact with the furnace atmosphere in the furnace chamber 2 and is conductingly connected with another electrode 11, which subsequently is referred to as the outer electrode. The electrodes 10 and 11 are made of platinum metals. The common contact position or point 12 between electrode, zirconium oxide and furnace atmosphere, and respectively, reference air, is effective as the measuring point.

In the embodiment form of the described device the outer electrode 11, at least at the contact point with the electrolyte is made from an electrically conducting element, which element does not act catalytically on or does not have a catalytic effect on a $CH_4$ disassociation. Herewith it is achieved in an advantageous manner that a reaction of bound oxygen continuing locally at the measuring point, as would correspond to the CO value of the furnace atmosphere, is avoided.

The special formation of the non-catalytically acting electrode 11 at the contact point with the solid electrolyte 9 comprises an electrically conducting material which contains at least 80% by weight of an element, the d-levels of the occupied electronic shells of which element are occupied completely with 10 electrons. Such elements for example are copper, silver, gold or paladium. With such a solid body electrolyte very precise measured values can be achieved with long service life or durability.

The method in accordance with the invention and the corresponding device are new, since for the first time they make possible an exact continuous measurement of the carbon level in gas mixtures which are not in the equilibrium condition. The method of the invention is exceptionally advanced since the simple admixing of fuels or combustion materials with a gas mixture (preferably air) containing bound or free oxygen in a furnace chamber permits the increase and control of the carbon level. Energy consuming devices for the production of controllable furnace atmospheres which are in the equilibrium condition are done away with or unnecessary. Moreover customary fuels in commercial use without definite or defined composition can be used.

We claim:

1. A method for control of the carbon level of a gas mixture reacting in a heat treatment furnace, comprising the steps of introducing a fuel containing hydrocarbon as a combustion gas as well as air into a furnace chamber to form a gas mixture by feeding exclusively flow streams of the combustion gas and the air into the furnace chamber, respectively, with the reaction products of the gas mixture not being in a state of water-gas equilibrium and not in a state of methane gas equilibrium and which gas mixture contains an excess of methane so as to assure an adequate supply of carbon, determining the controlled carbon level from measurement of the portion of the gas component CO which is present in the furnace chamber as a first measured value, from measurement of the electrical voltage of an oxygen-ion-conducting solid body electrolyte as a second measured value and from the furnace chamber temperature as a third measured value by feeding the three measured values to a computer and determining therein the carbon level from the three measured values, and controlling the carbon level dependent on this determination by changing the quantity flow of the combustion gas and/or of the air introduced into the furnace chamber until correspondence of the determined carbon level with its desired value is produced.

* * * * *